United States Patent [19]

Saxer et al.

[11] Patent Number: 5,504,247
[45] Date of Patent: Apr. 2, 1996

[54] METHOD AND APPARATUS FOR PURIFYING ACRYLIC ACID, AND ACRYLIC ACID PURIFIED BY THE METHOD

[75] Inventors: Kurt Saxer; Ralph Stadler, both of Buchs, Switzerland

[73] Assignee: Sulzer Chemtech AG, Winterthur, Switzerland

[21] Appl. No.: 216,162

[22] Filed: Mar. 22, 1994

[30] Foreign Application Priority Data

Mar. 26, 1993 [CH] Switzerland .................. 922/93

[51] Int. Cl.$^6$ ............................................. C07C 51/42
[52] U.S. Cl. ................................................ 562/600
[58] Field of Search ................................ 562/600

[56] References Cited

U.S. PATENT DOCUMENTS

| | | |
|---|---|---|
| 2,868,830 | 10/1954 | Weedman et al. . |
| 2,885,431 | 5/1959 | Tarr . |
| 3,050,952 | 8/1962 | Marwil . |
| 4,493,719 | 1/1985 | Wintermantel et al. . |
| 4,780,568 | 10/1988 | Pascoe ............................ 562/599 |

FOREIGN PATENT DOCUMENTS

| | | |
|---|---|---|
| 0002612 | 11/1982 | European Pat. Off. . |
| 1079676 | 11/1954 | France . |
| 1620756 | 7/1970 | Germany . |

OTHER PUBLICATIONS

Chemical Abstract 90:104686 1978.

*Primary Examiner*—Paul J. Killos
*Attorney, Agent, or Firm*—Frishauf, Holtz, Goodman, Langer & Chick

[57] ABSTRACT

A method of purifying acrylic acid by fractional crystallization is provided. The method includes the steps of subjecting an acrylic acid containing mixture to a dynamic crystallization stage to recover purified acrylic acid, leaving a residue containing acrylic acid; subjecting the residue to a static crystallization stage to recover an acrylic acid enriched fraction; and recycling the acrylic acid enriched fraction to the dynamic crystallization stage for recovery of purified acrylic acid.

15 Claims, 4 Drawing Sheets

METHOD AND APPARATUS FOR PURIFYING ACRYLIC ACID, AND ACRYLIC ACID PURIFIED BY THE METHOD

The invention relates to a method and apparatus for purifying acrylic acid by fractional crystallization.

In the plastics industry, acrylic acid is an important starting substance for textile fibers, surface coatings, adhesives etc. The annual output of acrylic acid and acrylic acid esters is several hundred thousand tons in each case.

Among the various known methods of production (acryl nitrile hydrolysis, catalytic conversion of acetylene with carbon monoxide and water etc) single-stage and two-stage heterogeneous catalytic oxidation of propene to acrylic acid via acrolein have become important recently. Owing to the different reaction conditions and the use of different catalysts, two-stage oxidation has a better yield—somewhat over 90%—than single stage oxidation. By contrast, the yield from single-stage oxidation is only about 60%.

Catalytic oxidation of propene to acrylic acid occurs at temperatures between 200° and 300° C. in the gas phase. The acrylic acid is then somewhat cooled and dissolved in a solvent such as water or a high-boiling ester. Subsequent purification, e.g. by distillation, yields acrylic acid with about 99% purity. Pure acrylic melts at 13.5° C. and boils at 141.6° C. at normal pressure (760 Torr).

Some impurities such as acrolein or propionic acid cannot be completely removed by distillation, and also acrylic acid easily polymerizes during distillation, and consequently other methods of purifying acrylic acid, such as fractional crystallization, have recently been proposed. The usefulness of fractional crystallization for purifying acrylic acid in aqueous solution is limited, however, in that acrylic acid forms a eutectic with water at a 63% content of acrylic acid by volume. In EP-0 002 612 therefore it is proposed to add salts to the aqueous solution in order to break up the eutectic.

DE-OS 26 06 364 discloses a method of fractional crystallization for purifying compounds melting at between −50° to +200° C. In this method the compounds are sent in a turbulent flow through a permanently filled crystallization zone and left at the crystallization temperature until a freezing-out rate of 70 to 98% is reached. This method has the disadvantage that the efficiency of separation decreases as soon as the proportion of impurities reaches about 20 to 30% by weight. This method of purification therefore yields a large quantity of residue which has to be disposed of or otherwise processed.

In fractional crystallization, a distinction can be made between static and dynamic crystallization. In dynamic crystallization of the falling-film or fully flowed-through tube type, the crystals grow on a cooled wall along which a solution or melted mixture of product is conveyed. The heat of crystallization is dissipated by the crystal layer which forms and which is cooled from the exterior, resulting in high-speed crystallization.

In the previously-mentioned dynamic crystallization process, the efficiency of separation for purifying acrylic acid decreases when the content of product is in the range of 70 to 80% by weight. The reason is that acrylic acid containing between 20 and 30% impurities crystallizes out in unfavorable, i.e. dendritic shapes, and the crystal layers are spongy and soft. In comparison with their volume, the crystal layers have a large surface area, resulting in large wetting surfaces and additional high retention of liquid. Consequently, relatively large amounts of residue occur during purification by dynamic crystallization. The residues have to be disposed of in conformity with strict modern environmental regulations. Usually the residues are not economic to process, owing to the different compounds occurring therein.

In static crystallization, the compound for purification is crystallized out on cooling surfaces projecting into a tank. The disadvantage of fractional static crystallization compared with falling-film crystallization is that in order to obtain a given capacity, the static crystallizer must be made larger than a corresponding dynamic crystallizer, because the crystallization process is slower. Static crystallization therefore is not an economic method of purifying acrylic acid on a large industrial scale. Since also, as known and as already mentioned, the crystal layers become worse, i.e. softer and spongier, the higher the content of impurities, static-crystallization has not hitherto been under consideration as a method of purifying acrylic acid.

In fractional suspension crystallization the solution or melt is cooled below the saturation temperature, so that crystals begin to form. The driving force of crystallization is the extent to which the solution is supersaturated. The resulting heat of crystallization is dissipated through the liquid phase. One disadvantage of suspension crystallization is the time taken, which is longer than in the previously-mentioned methods, so that this method is less economical.

BRIEF DESCRIPTION OF THE INVENTION

An object of the present invention is to provide an improved, eco-friendlier and less expensive method of purifying acrylic acid, at least partly avoiding the initially-mentioned disadvantages and more particularly reducing the amount of residues to be disposed of and increasing the output of pure acrylic acid.

According to the invention, this is achieved by a method in which acrylic acid is purified in a number of stages by a combination of dynamic and static crystallization, the residue from dynamic crystallization being further purified by static crystallization and the resulting acrylic acid being returned to dynamic crystallization. It has unexpectedly been found that static crystallization, if the process is suitably controlled, can yield crystal layers which can be kept sufficiently stable to allow removal even if the impurity content is up to about 50% by weight, i.e. a range in which dynamic crystallization ceases to be efficient. Since the crystal layers adhere to the cooling surfaces of the static crystallizer, contrary to expectation, good separating efficiency can be obtained at the aforementioned high content of impurities. Consequently additional acrylic acid can be obtained from the residue, which would otherwise have to be dumped or processed by other methods. A considerable reduction can therefore be made in the amount of residue from the purification process.

Acrylic acid containing up to 20%, preferably up to 10% of impurities by weight is preferably supplied to a dynamic crystallization stage and purified in two or more stages by crystallization/melting cycles in a dynamic crystallizer. The crystallized substance from the highest stage of the dynamic crystallizer can leave the purification process. In the lowest stage of dynamic crystallization, the impurities in the residue can be concentrated to up to about 30%, preferably 10% to 25%, by weight, and used as a feed for static crystallization, in which the residue is purified in at least one stage. The impurities in the residue leaving the purification process can thus be concentrated to about 70% by weight. The crystallized material obtained by static crystallization in the highest stage can then be returned to dynamic crystallization. This is an efficient, economic process. A specially important point, with regard to the usefulness of this process, is that the composition of the feed for the static crystallizer is optimal. It has been shown that the qualitative composition of the feed is important, as well as the content of impurities. It has been found that if, for example, straight-chain saturated carboxylic acids such as acetic acid and propionic acid constitute most of the impurities, the crystal layers can become soft and spongy even at a low content of impurities. If the content of impurities in the lowest stage of dynamic crystallization is concentrated to 20–30% by weight, static crystallization does not yield satisfactory results, because the crystal layers do not adhere sufficiently to the cooling surface. Dynamic crystallization must therefore be stopped on reaching a certain content of impurities, depending on the qualitative composition thereof, even though more acrylic acid could be obtained from the residue by dynamic crystallization. By this means, a first stable firmly-adhesive crystal layer with advantageous crystal shapes can form on the cooling surfaces of the static crystallizer. This then forms the foundation for further crystal layers.

Since the cooling surfaces are still moistened with melt after the crystal layer melts, they are advantageously frozen out before the static crystallizer is filled with new, less pure acrylic acid from the next lower stage. This procedure can form another firmly-adhesive crystal layer, so that an additional stage in the static crystallizer can be operated.

Another advantage of the process is that acrylic acid can be purified even if the content of impurities by weight is high, up to about 20%. Usually, however, acrylic acid produced nowadays by oxidation of propene and pre-purified by distillation contains less than 5% by weight of impurities.

Advantageously the residue in dynamic crystallization and the partial melt from a particular stage are additionally purified in a respective lower stage of dynamic crystallization in a subsequent sequence. The partial melt from the lowest stage of dynamic crystallization is advantageously purified again in the same stage. This is a simple process, whereby the impurities in the lowest stage are concentrated up to about 30% by weight.

Advantageously static and dynamic crystallization occur simultaneously side by side, i.e. batches with a lower content of impurities are purified in the dynamic crystallizer at the same time as batches with a high content of impurities are subjected to a crystallization and melting cycle in the static crystallizer. This is time-saving and economical.

Advantageously the partial melt from the highest stage of static crystallization is divided into two parts. The first part can be purified in the next-lower stage and the second part in the same stage of a subsequent sequence. This increases the separating efficiency of static crystallization, since the second part of the partial melt is considerably purer than the first part.

Advantageously in static crystallization the heat transfer medium in the crystallization phase is left at the starting temperature of about 0° to 15° C. for about an hour and then cooled to the final temperature of about −30° to −15° C. for about 5 to 6 hours. This is important, since the constant temperature of the heat transfer medium in the starting phase can result in advantageous crystal shapes having a lower content of impurities and also sufficiently stable to prevent the crystal layers flaking off the cooling surfaces.

In the highest stage of dynamic crystallization, advantageously only the crystallized material from the previous stage is fed in. This has a strongly purifying effect.

Advantageously acrylic acid is purified by static crystallization in two stages. This can increase the proportion of impurities in the residue to about 70% by weight.

Advantageously the partial melt from the first stage of static crystallization is purified in the same stage, and the corresponding crystallized material is additionally purified in the second stage of a subsequent sequence. Advantageously the dynamic crystallization is of the falling-film or fully flowed-through tube type. Both methods are particularly efficient and fast. To obtain higher than 99.9% purity, the acrylic acid is advantageously purified by dynamic crystallization in five stages. To obtain even higher purity, the number of stages can be increased.

Advantageously no new material is added to at least one additional stage of dynamic crystallization. This can happen e.g. if a relatively pure feed product is used, thus saving a tank and reducing the cost of the plant.

Advantageously the acrylic acid is purified by a combination of suspension crystallization and static crystallization, the residue from suspension crystallization being further purified by static crystallization and the resulting acrylic acid being returned to suspension crystallization.

Advantageously acrylic acid containing up to 20%, preferably up to 10% of impurities by weight is supplied to a suspension crystallization stage and purified in one or more stages in crystallization/melt cycles. The crystallized material from the highest stage can leave the purification process. In the lowest stage of suspension crystallization, the impurities in the residue are concentrated to about 30%, preferably 10% to 25%, by weight and the residue is used as the feed for static crystallization. The static crystallization process can be controlled as previously described.

BRIEF DESCRIPTION OF THE DRAWINGS

The method and apparatus will now be described with reference to the drawings, in which:

FIG. 1 shows a purification apparatus comprising a dynamic crystallizer K-1 and a static crystallizer K-2. Tanks T-1 to T-5 are for temporary storage of acrylic acid which, after a crystallization and melting cycle, is transferred in the form either of residue R, partial melt S or crystallized material C to a suitable tank. The contents of tanks T-1 to T-5, after temporary storage, are supplied to a suitable purification stage of static crystallization or dynamic crystallization in a subsequent sequence. The tank T-6 is a buffer tank and receives the purified acrylic acid.

DETAILED DESCRIPTION OF THE INVENTION

The acrylic acid is pumped by a respective pump P-0 to P-5 from the tanks T-1 to T-5 to the crystallizers K-1 and K-2. During the crystallization phase, the melt flows out of the bottom of crystallizer K-1 and is recycled by pump P-2 to the top of the crystallizer.

The dynamic crystallizer K-1 comprises a bunch of tubes in a jacket and supplied with a trickling film or a full-tube flow of feed product F for purification. The bunch of tubes are externally surrounded by a heat transfer medium which removes the heat produced during crystallization. The temperature of the heat transfer medium, depending on the purification stage and the phase of the crystallization process, lies in a certain range below or above the solidification point (the crystallization or melting phase) of the compound to be purified. A detailed description of a dynamic crystallizer can be found in U.S. Pat. No. 3,621,664 by K. Saxer.

The static crystallizer K-2 comprises a tank with an inlet and an outlet for the feed product F. Cooling surfaces flowed through by a heat transfer medium dip into the tank.

Figure 1:
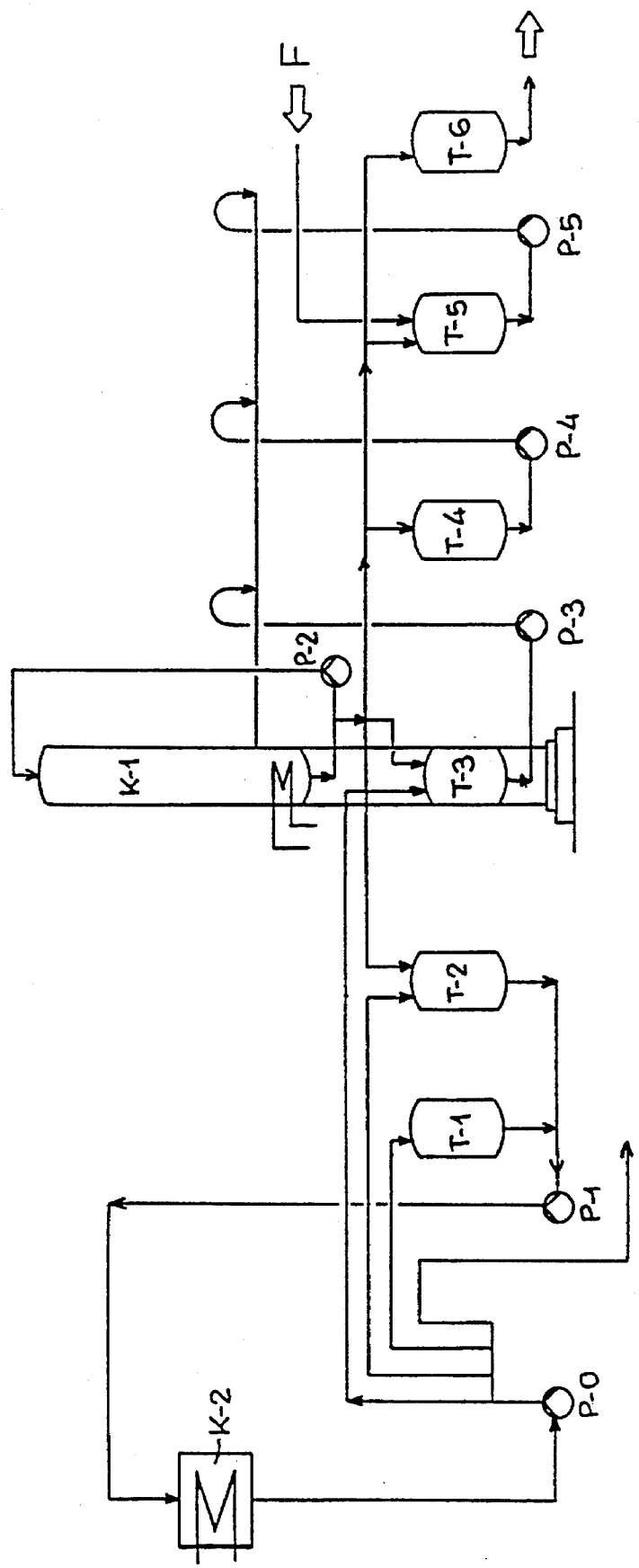
FIG. 1 shows a purification apparatus comprising a static crystallizer and a dynamic crystallizer.
Figure 2:
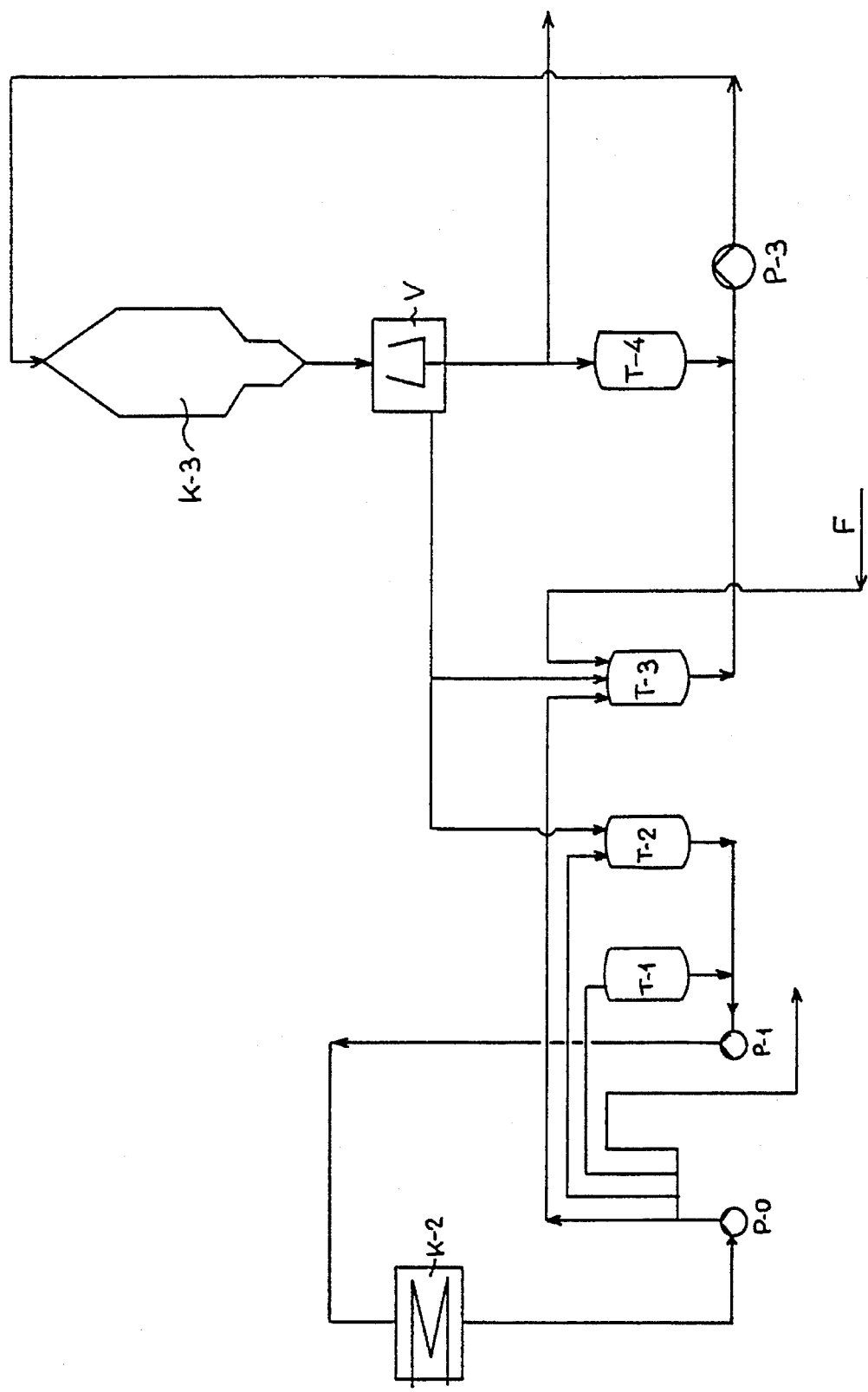
FIG. 2 shows a purification apparatus comprising a static crystallizer and a suspension crystallizer.

FIG. 2 is a diagram of a purification apparatus comprising a suspension crystallizer K-3 and a static crystallizer K-2. The suspension crystallizer K-3 comprises a tank having an inlet and an outlet, followed by a device V for separating the crystals. The crystals are transferred to tank T-4 or discharged as a pure product, and the mother liquor, depending on the stage, can be conveyed either to tank T-2 or T-3. As in the purification process in FIG. 1, the static crystallizer K-2 can be associated with two tanks T-1 and T-2. Depending on the content of impurities in the acrylic acid and the desired purity thereof, the device can differ from the previous example, e.g. by being equipped with a larger or smaller number of tanks.

The Process

Figure 3:
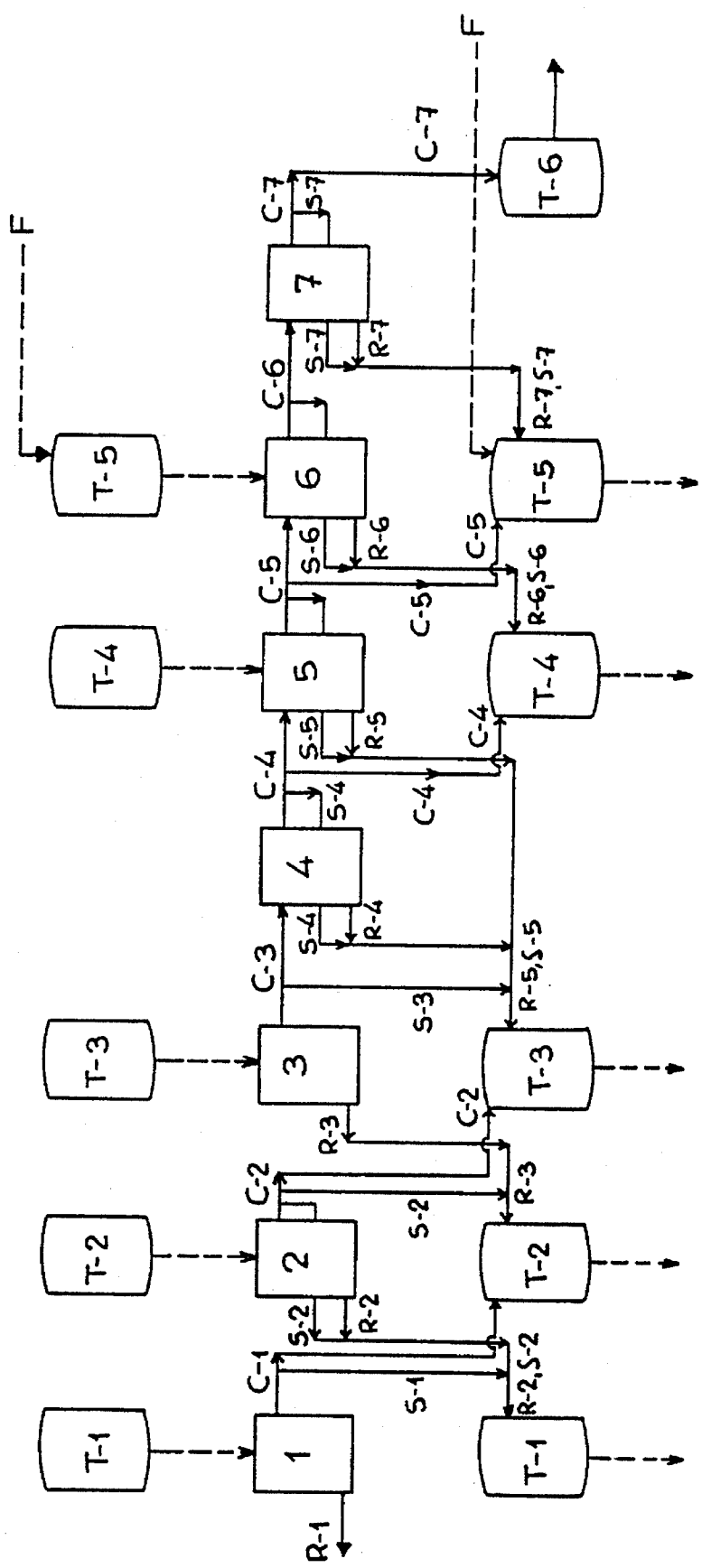
FIG. 3 is a flow chart of acrylic acid for purification with a purity of above 99% during the purification process.

The purification of acrylic acid by the process according to the invention will now be described with reference to the flow diagram in FIG. 3. The following percentages are by weight. To obtain purity of above 99.9% and a content of impurities of about 40–70% by weight in the residue, the acrylic acid is purified by a static and a dynamic crystallizer in seven stages. The individual stages correspond to different degrees of purity and are marked 1 to 7. Note that the stage numbers 1 to 7 relate not to a particular physical part of the crystallizers but to an operation in the process sequence.

Purification by static crystallization is brought about in stages 1 and 2, where the highest concentrations of impurities occur, whereas purification by dynamic crystallization occurs in the subsequent stages. The FIGS. 1, 2 and 3 etc. at the rear denote the residue R, the partial melt S and the crystallized material C from the respective purification stages 1, 2, 3 etc. The feed product F, depending on its purity, is sent to a purification stage containing a mixture having a similar composition to the feed product.

In the case of purification of a feed product which has already been partly purified, e.g. by distillation, and has a purity of over 99%, the liquid acrylic acid F is fed to tank T-5, where a part of the crystallized material C-5 from the fifth stage, the residue R-7 and the partial melt S-7 are also collected. The contents of tank T-5 serves as a feed for the sixth purification stage, together with part of the molten crystallized material C-5 from the fifth stage, if a fifth stage is operated before the sixth. Note that in this example the stages do not all occur in sequence; stages 5, 6 and 7, for example, may operate more frequently. Less pure acrylic acid accumulates, e.g. in tank T-3, until a full batch for the dynamic crystallizer has been obtained (Table 3).

The pump P-5 pumps the contents of tank T-5 to the bottom part of the crystallizer K-1 and from there by pump P-2 to the top of crystallizer K-1 and the acrylic acid is uniformly distributed among the individual tubes (FIG. 1). A heat-transfer medium simultaneously flows around the exterior of the tubes. Along the inside of the tubes, the acrylic acid flows in a falling film or fills the entire tube. By means of the pump P-2, the acrylic acid flowing out at the bottom of the crystallizer K-1 is returned to the top and distributed among the tubes. The heat transfer medium is then rapidly cooled to a temperature which, depending on the stage, can be about 5° to 20° C. below the solidification point of acrylic acid. The acrylic acid then begins to crystallize out in a layer on the inside of the tubes. The resulting heat is dissipated through the crystal layer and the heat transfer medium flowing along the outer walls. The heat transfer medium is then additionally cooled, slowly and continuously. When the crystal layer reaches a certain thickness, the pump P-2 is switched off and the residue R-6 is discharged into the tank T-4.

The next step is the "sweating phase". To this end the temperature of the heat transfer medium is raised until the crystal layer partly melts. In the process the impurities adhering to the surface and enclosed in the crystal layer are partly melted or dissolved out. The partial melt S-6 formed during the sweating phase in the sixth stage is conveyed to the tank T-4. The crystal material C-6 is then melted and directly fed to the seventh purification stage. In contrast to the sixth stage, therefore, no new material is added to the seventh purification stage, which is therefore also called a "half-stage". An additional crystallization/melting cycle follows, the residue R-7 and the partial melt S-7 being conveyed to tank T-5. The crystallized material C-7 in the form of pure product leaves the purification circuit and is temporarily stored in tank T-6 before removal.

In the fifth purification stage the contents of tank T-4 is pumped into the crystallizer K-1, which contains any molten crystallized material C-4 remaining from the fourth stage. The contents of tank T-4 is made up of the residue R-6, the partial melt S-6 and some of the crystallized material C-4 from the previous sequence.

The residue R-5 and the partial melt S-5 from the fifth stage are introduced into tank T-3. Some of the molten crystallized material C-5 enters the tank T-5, whereas the rest of the crystallized material C-5, together with fresh product F and the contents of tank T-5 in the previous sequence, serves as the feed for the sixth purification stage.

It has been found advantageous to divide the crystallized material C-4, C-5 from stages four and five and introduce part of it into the tank supplying the next higher stage. This balances the concentrations and mass ratios, so that the sixth stage can always be supplied with the same quantity of fresh feed product F, which is a help in automating the process. In addition, the acrylic acid leaving the purification process is of constant quality.

Stages 3 and 4, likes stages 6 and 7 are operated directly in succession, i.e. in this example the fourth stage is, like stage 7, a "half-stage" not supplied with new material. Accordingly, only the crystallized material from the previous stage is supplied to this half-stage. The feed for the third stage is the contents of tank T-3, in which the residues R-4, R-5 and the partial melts S-3, S-4, S-5 are collected together with the crystallized material C-2 from the second stage. The residue R-3 from the third stage is supplied to tank T-2.

In stage 2, the acrylic acid is purified preferably by static crystallization. The feed is supplied by tank T-2, which contains the molten crystallized material C-1, the residue R-3 from dynamic crystallization and the second part of the partial melt S-2 from the static crystallizer K-2. The separating efficiency in the static crystallizer K-2 can be increased by dividing the partial melt S-2 into two parts. The first part, which contains a higher concentration of impurities, is preferably supplied to tank T-1 in the lower first stage, whereas the second part is supplied to tank T-2 in stage 2.

The contents of tank T-2 is pumped into the static crystallizer K-2, where some of the acrylic acid crystallizes on the heat-exchanger plates dipping into the melt. After a certain time the non-crystallized melt in the form of residue R-2 is transferred to tank T-1. The first part of the partial melt S-2 is also supplied to tank T-1, whereas the second part is supplied to tank T-2.

In the first stage, the contents of tank T-1 is processed. The residue R-1 leaves the circuit, whereas the partial melt S-1 is introduced into tank T-1 and the crystallized material into tank T-2.

As shown in the flow diagram (FIG. 3), the flow of material is in opposite directions, the purity of the acrylic acid increasing from left to right. The individual process stages are run through in a sequence always from bottom to top, i.e. from less pure to purer product. The residues, the partial melts and any molten crystallized material from the individual stages are temporarily stored in tanks T-1 to T-5 and re-used in a subsequent sequence. The crystallized material C-3 to C-6, except for a part which is melted to balance the mass ratios and concentrations, remains in the crystallizer K-1 and is subjected to another crystallization/melting cycle in a next-higher stage, either alone (stage 4 and 7) or together with temporarily stored acrylic acid from one or more previous sequences. In the static crystallizer K-2 the crystal material C-1 and C-2 is transferred to tank T-2 or T-3 after melting.

If the aforementioned method is used to purify a feed product containing a higher content of impurities, the feed product is introduced into a tank having a composition corresponding approximately to that of the feed product.

The method of purifying acrylic acid using a suspension crystallizer is basically the same as previously described. However, when the purification device in FIG. 2 is used, a smaller number of stages, e.g. four, can be provided. The feed product F is introduced into the tank T-3 and then conveyed by pump P-3 to the suspension crystallizer K-3, where the acrylic acid begins to crystallize out (stage 3). After a certain time, the process is stopped and the crystals are separated from the mother liquor in the separating device V. The filtered crystals are then melted and the melt is temporarily stored in tank T-4. The mother liquor is introduced into tank T-2, the contents of which is purified by the static crystallizer, e.g. in two stages. Stage 3 is repeated until sufficient material for the fourth stage is available. The crystal material from the fourth stage can then leave the purification process, and the residue from this stage is introduced into tank T-3, which also receives the acrylic acid purified by static crystallization.

The following are examples of purification of acrylic acid by the process.

EXAMPLE 1

The feed product was previously-purified acrylic acid containing 99.67% of product. The acrylic acid was purified as per the flow diagram in FIG. 3. The proportions by weight of impurities in the feed product, the purified product and the residue are shown in Table 1. The proportion of impurities at the interface between dynamic and static crystallization was about 12 to 15%.

TABLE 1

| Composition of the feed product, the final product and residue | | | |
|---|---|---|---|
| | Feed product [%] | Product [%] | Residue [%] |
| Acrylic acid | 99.628 | 99.938 | 62.79 |
| Acetic acid | 0.223 | 0.038 | 22.21 |
| Propionic acid | 0.028 | 0.006 | 2.64 |
| Dimer | 0.009 | 0.001 | 0.96 |
| Aldehydes | 0.025 | 0.000 | 3.00 |
| Water | 0.057 | 0.017 | 4.81 |
| Phenothiazine | 0.030 | 0.000 | 3.59 |

Table 2 shows the initial temperature Ts and the final temperature Te of the heat transfer medium during the sweating phase and the crystallization phase. In the stated time intervals Δt the heat transfer medium is uniformly cooled from the initial temperature Ts to the final temperature Te. In the static crystallizer K-2 the heat transfer medium is advantageously left at the initial temperature for 1 hour at the beginning of the cooling phase, to prevent unduly rapid crystallization. This is particularly important in preventing the formation of disadvantageous crystal shapes, e.g. dendritic crystals. At the end of the cooling phase the heat transfer medium is left at the final temperature Te, preferably for between 2 and 3 hours. In order to melt the crystallized material, the heat transfer medium is heated to about 35° C. The melting phase lasts about one hour in the static crystallizer and about 15 minutes in the falling-film crystallizer. The solidification point of the acrylic acid rises from 5° C. in stage 3° to 13° C. in stage 7. The output of acrylic acid with more than 9.9% purity is 99.5% relative to the feed product. The residue has a content of only 62.8% acrylic acid.

TABLE 2

| Temperature of heat transfer medium during the sweating and crystallization phase | | | | | | |
|---|---|---|---|---|---|---|
| Step | Sweating phase | | | Crystallization phase | | |
| | $T_s$ | $T_e$ | Δt[min$^{-1}$] | $T_s$ | $T_e$ | Δt[min$^{-1}$] |
| 1 | 0 | 10 | 120 | −15 | −30 | 420 |
| 2 | 0 | 10 | 120 | 0 | −15 | 360 |
| 3 | −5 | 5 | 20 | −5 | −25 | 70 |
| 4 | 0 | 13 | 20 | 0 | −25 | 50 |
| 5 | 7 | 18 | 20 | 3 | −22 | 60 |
| 6 | 12 | 15 | 20 | 4 | −20 | 50 |
| 7 | 15 | 16 | 15 | 5 | −10 | 25 |

In the dynamic crystallizer, the following sequence of stages for purification of acrylic acid have been found advantageous:

TABLE 3

| Sequence of purification stages | | |
|---|---|---|
| | Dynamic crystallizer | Static crystallizer |
| Beginning | 3, 4, 5, 6, 7 | |
| | 6, 7 | 1 | Total |
| | 5, 6, 7 | | run-through |
| | 6, 7 | | time: |
| | 5, 6, 7 | 2 | Approx. 21 hours |
| | 6, 7 | | |
| Beginning | 3, 4, 5, 6, 7 | |
| | — | 1 | |

EXAMPLE 2

Figure 4:
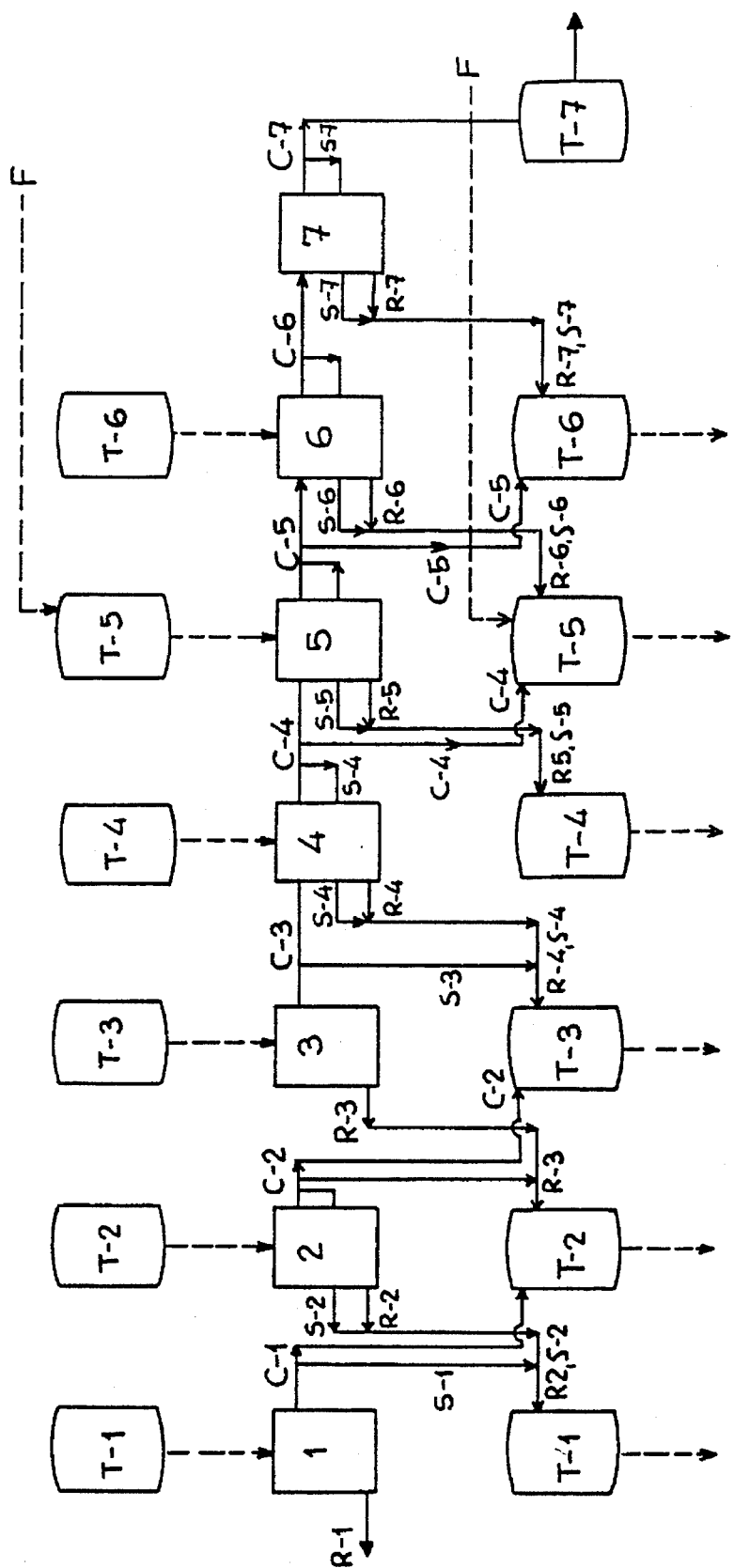
FIG. 4 is a flow diagram of acrylic acid to be purified with a purity of about 97.8% during the purification process.

The feed product was previously purified and contained 97.8% acrylic acid. The acrylic acid was purified as per the flow diagram in FIG. 4. The differences from the method in FIG. 3 are as follows: owing to the lower purity of the feed product, it was supplied to stage 5, which had approximately the same composition. The difference in starting concentration resulted in different mass ratios, so that stage 4 could be operated as a full stage, i.e. an additional tank T-4 was used for the fourth stage, in contrast to the first example. The proportions by weight of impurities in the feed product, the purified product and the residue are shown in Table 4.

TABLE 4

Composition of the feed product, the final product and the residue

| | Feed product [%] | Product [%] | Residue [%] |
|---|---|---|---|
| Acrylic acid | 97.771 | >99.933 | 52.2 |
| Acetic acid | 0.250 | 0.018 | 5.14 |
| Propionic acid | 0.021 | 0.005 | 0.36 |
| Dimer | 0.7 | 0.027 | 14.88 |
| Aldehydes | 0.028 | 0.000 | 0.62 |
| Water | 1.2 | 0.017 | 26.14 |
| Phenothiazine | 0.03 | 0.000 | 0.66 |

The initial temperatures Ts and the final temperatures Te of the heat transfer medium during the sweating phase and the crystallization phase, and the individual time intervals Δt during which the heat transfer medium was cooled from the initial temperature Ts to the final temperature Te, substantially agree with those in Example 1. In the dynamic crystallizer, the following sequence of stages for purifying acrylic acid were found advantageous:

TABLE 5

Sequence of purification stages

| Dynamic crystallizer | Static crystallizer | |
|---|---|---|
| Beginning  3, 4, 5, 6, 7 | | |
| 5, 6, 7 | 1 | Total |
| 4, 5, 6, 7 | | run-through |
| 5, 6, 7 | | time: |
| 4, 5, 6, 7 | 2 | Approx. 28 hours |
| 5, 6, 7 | | |
| Beginning  3, 4, 5, 6, 7 | | |
| — | 1 | |

We claim:

1. A method of purifying acrylic acid by fractional crystallization comprising the steps of subjecting an acrylic acid containing mixture to a dynamic crystallization stage to recover purified acrylic acid, leaving a residue containing acrylic acid;

subjecting the residue to a static crystallization stage to recover an acrylic acid enriched fraction; and recycling the acrylic acid enriched fraction to the dynamic crystallization stage for recovery of purified acrylic acid;

wherein acrylic acid containing up to 20% by weight of impurities, is supplied to the dynamic crystallization stage and the acrylic acid is purified in two or more stages by crystallization/melting cycles in a dynamic crystallizer, the crystallized material from the highest stage being recovered as the purified acrylic acid, and in the lowest stage of dynamic crystallization the impurities in the residue are concentrated to up to about 30%, the residue being subjected to the static crystallization, in which the residue is purified in at least one stage, whereby the impurities in waste leaving the static crystallization of the purification process can be concentrated to up to about 70% by weight, and the crystallized material acrylic acid enriched fraction from the highest stage of the static crystallization is recycled to the dynamic crystallization stage; and wherein the dynamic crystallization is of the falling-film or fully flowed-through tube type.

2. The method according to claim 1, wherein the feed of arylic acid contains up to 10% by weight impurities and the impurities in the residue are concentrated to about 10% to 25% in the dynamic cystallizer.

3. The method according to claim 1, wherein the residue in dynamic crystallization and the partial melt from a given stage are each additionally purified in a lower stage of dynamic crystallization in a subsequent sequence, and the partial melt from the lowest stage of dynamic crystallization is re-purified in the same stage.

4. The method according to claim 1, wherein the partial melt from the highest stage of static crystallization is divided into two parts, the first part being purified in the next lower stage and the second part in the same stage of a subsequent sequence.

5. The method of claim 1, wherein the static crystallization comprises maintaining the heat transfer medium in the crystallization phase at a starting temperature of about 0° to −15° C. for about 1 hour and then cooling to a final temperature of about −30° to −15° C. for about 5 to 6 hours.

6. The method according to claim 1, wherein in the highest stage of dynamic crystallization, only the crystallized material from the previous stage is used.

7. A method according to claim 1, wherein the acrylic acid is purified by static crystallization in two stages.

8. The method according to claim 7, wherein the partial melt from the first stage is purified in the firsts stage of a subsequent sequence and the corresponding crystallized material is purified in the second stage thereof.

9. A method according to claim 1, wherein in order to obtain purity above 99.9%, the acrylic acid is purified by dynamic crystallization in five stages.

10. The method according to claims 9, wherein no new material is added in at least one additional stage of dynamic crystallization, i.e. the stage is operated as a half-stage.

11. A method of purifying acrylic acid by fractional crystallization, wherein acrylic acid is purified by a combination of suspension crystallization and static crystallization in a number of stages, the residue from suspension crystallization being further purified by static crystallization and the resulting enriched acrylic acid being returned to suspension crystallization; and wherein acrylic acid containing up to 20% by weight of impurities is supplied to a suspension crystallization stage and the acrylic acid is purified in one or more stages in crystallization/melt cycles, the crystallized material from the highest stage leaving the purification process, and in the lowest stage of suspension crystallization the impurities in the residue are concentrated to up to about 30%, the residue serving as a feed for static crystallization, in which the residue is purified in at least one stage whereby the impurities in the residue leaving the purification process can be concentrated to up to about 70% by weight and the crystallized material obtained from the highest stage of static crystallization is returned to dynamic crystallization.

12. The method according to claim 11, wherein in the dynamic crystallization process the heat transfer medium, depending on the purity of the melt, is cooled from about 5° to −5° C. to about −10° to −25° C. during the crystallization phase and heated to up to about 18° C. during the sweating phase.

13. The method according to claim 1, further comprising the step after the crystal layer formed on the cooling surfaces of the static crystallizer has melted and after the melt has been discharged into a tank, of cooling the crystallizer whereby the melt still adhering to the cooling surfaces is crystallized out to form a stable crystal layer before the crystallizer is filled with a new batch.

14. A method according to claim 1, wherein the impurities are concentrated to about 10% to 25% in the dynamic crystallizer.

15. A method according to claim 1, wherein static and dynamic crystallization occur simultaneously.

* * * * *